United States Patent [19]

Weis

[11] Patent Number: 5,075,433

[45] Date of Patent: Dec. 24, 1991

[54] SUBSTITUTED-3-SULFATOGLUCURONIC ACID ANTIGENS

[75] Inventor: Alexander L. Weis, Rochester, N.Y.

[73] Assignee: Eastman Kodak Company, Rochester, N.Y.

[21] Appl. No.: 229,054

[22] Filed: Aug. 5, 1988

[51] Int. Cl.$^5$ .............................................. C07M 11/00
[52] U.S. Cl. ...................... 536/118; 536/4.1; 536/119; 536/122; 530/387; 514/25; 206/569
[58] Field of Search ............... 536/4.1, 17.2, 17.5, 536/17.6, 17.9, 118, 122, 119

[56] References Cited

U.S. PATENT DOCUMENTS 4,137,401  4/1979  Lemieux et al. ..................... 536/116
4,238,473  11/1980  Lemieux et al. ...................... 424/11

OTHER PUBLICATIONS

Chou et al. (1986) J. of Biol. Chem 261:11717–11725.
Chou et al. (1985) Biochem. Biophys. Res. Commun. 128:383–388.
Ariga et al. (1987) J. of Biol. Chem. 262:848–853.

*Primary Examiner*—Johnnie R. Brown
*Assistant Examiner*—Elli Peselev
*Attorney, Agent, or Firm*—Dressler, Goldsmith, Shore, Sutker & Milnamow, Ltd.

[57] ABSTRACT

A novel 3-sulfatoglucuronic acid-containing compound is produced. A method for antibody removal from a liquid sample, and a method of treatment for antibody-related disorders is disclosed, along with a diagnostic kit.

2 Claims, No Drawings

SUBSTITUTED-3-SULFATOGLUCURONIC ACID ANTIGENS

The present invention relates to synthetic sulfatoglucuronic acid compounds. The present invention also relates to pharmaceutical compositions containing a synthetic sulfatoglucuronic acid compound as an active ingredient. The present invention further relates to a treatment for peripheral neuropathies which comprises the use of a synthetic sulfatoglucuronic acid compound which can bind to specific antibody molecules. The sulfatoglucuronic acid compounds of the invention are utilized in an extracorporeal treatment method to remove specific antibody molecules from mammalian circulatory systems, such as from human blood. They are also used to diagnose disorders that are caused by or involve the presence of excessive concentrations in mammals of specific antibodies (e.g. peripheral neuropathies), and in diagnostic assays that can determine the presence in mammalian sera of excessive concentrations of the causative antibodies.

BACKGROUND OF THE INVENTION

Peripheral neuropathies are conditions resulting from injury to the peripheral nervous system. Patients with these conditions experience weakness and sensory loss, for example, eyelid droop (ptosis) from loss of control of muscles, and muscle deterioration. The cause of the neuropathy in many patients is unknown, but in some cases it is associated with plasma cell dyscrasia, where individual clones of antibody-producing cells proliferate abnormally and produce antibodies (IgM) in excess. These antibodies are derived from the same clones and are thus monoclonal antibodies, designated as M-proteins. (McLeod et al (1984) *Peripheral Neuropathy*, p. 1847-1865, edited by Dyck et al, Saunders, Philadelphia; Latov (1984) in Neuroimmunology, p. 261-273, edited by Behan et al, Raven Press, N.Y.).

In some patients with neuropathy and plasma cell dyscrasia there are high concentrations of IgM M-proteins. The M-proteins have been shown to react with myelin and myelin-associated glycoproteins (MAG) to cause demyelination of the myelin sheath. (Braun et al., J. Neurochem. 39:1261-1265 (1982); Steck et al, Neurology 33:19-23 (1983); Ilyas et al, Proc. Nat'l Acad. Sci., U.S.A. 81:1225-1229 (1984)).

To date, the most successful treatment for peripheral neuropathies has been plasmapheresis wherein the patient's blood plasma is removed and replaced. Recent studies have indicated that the M-proteins bind to a carbohydrate determinant shared by a number of peripheral nerve glycoproteins, including MAG, and by two acidic glycolipids in peripheral nerves. (Chou et al, Biochem. Biophys. Res. Commun. 128:383-388 (1985); Chou et al, J. Biol. Chem. 261:11717-11725 (1986); Ariga et al, J. Biol. Chem. 262:848-853 (1987)). These investigators have reported that the reactive glycolipids are not gangliosides and that M-proteins directed against MAG probably bind to the same or closely related carbohydrate determinants. The glycolipid antigen was characterized as a sulfated glucuronic acid-containing paragloboside; a paragloboside is a lacto-N-neotetraosyl ceramide. [Schwarting et al. J. Immunol 118:1415-1419 (1977)]. Glucuronic acid-3-sulfates containing oligosaccharides have been found to be antigenic for M-proteins and have been used in characterization studies to isolate the IgM M-proteins. These naturally occurring oligosaccharides are generally pentasaccharide-containing ceramides which contain a terminal 3-sulfated glucuronic acid moiety. [Chou et al, J. Biol. Chem. 261:11717-11725 (1986); Ariga et al, J. Biol. Chem. 262:848-853 (1987)]. Such antigenic oligosaccharides are difficult and expensive to purify and/or synthesize. The present invention provides relatively inexpensive, synthetic monosaccharides that mimic the antigenic activity of naturally occurring products such as the M-protein antigens.

SUMMARY OF THE INVENTION

The present invention relates to 3-sulfatoglucuronic acid-1-glycolipids having a structural formula as represented by:

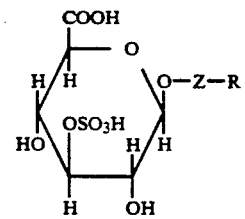

Formula (I)

where R is a reactive functional group and Z is a lipid tail, or physiologically acceptable derivatives thereof. The lipid tail contains a backbone chain of about 4 to about 30 atoms extending from the 1-position of the 3-sulfatoglucuronic acid to the R group. Carbon atoms or heteroatom spacers may be present in the backbone of the lipid tail. The heteroatom spacers are preferably sulfur, nitrogen or oxygen atoms. The lipid tail can contain physiologically tolerable substituents attached to it and can contain at least one unsaturated linkage.

Preferred compounds of the present invention are 3-sulfatoglucuronic acid containing compounds having a structural formula represented by:

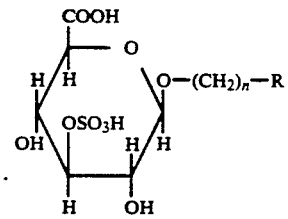

Formula (II)

and derivatives thereof, where n is an integer of about 4 to about 24, and R is a reactive functional group. Also contemplated as being within the scope of the present invention are 3-sulfatoglucuronic acids containing glycolipids wherein the alkylene chain designated in Formula II as $(CH_2)_n$ also has further physiologically acceptable substituents interspersed along the chain.

The present invention also relates to a coated support which is produced by attaching a compound of Formula I to a solid support. The coated support is preferably produced by chemically attaching a compound of Formula I through the reactive functional group R to an inert, immobile solid support material such as glass, ceramic or polymer resins.

A method for the removal of an antibody that possesses affinity for a compound of Formula I is further contemplated. In this method, a coated support is contacted with a liquid sample for a time period sufficient to allow antibodies, which possess affinity for the attached molecule of Formula I, to bind to the coated support; the coated support is then separated from the liquid sample, thus removing the bound antibodies from the sample. Further washing of the coated support and assaying for the presence of the bound antibodies is also contemplated. It is preferentially contemplated that the antibodies bound to the coated support are the M proteins which bind to myelin associated glycoproteins.

A method of treatment for antibody-related disorders is further contemplated in the present invention. This method involves the removal of blood from the circulatory system of a host mammal and the extracorporeal contacting of this blood with an immobilized coated support that contains, attached thereto, compounds of Formula I. The coated support and blood are maintained in contact for a time period sufficient for antibodies present in the blood, that possess affinity for the coated support, to bind to the coated support to produce a "treated blood". The "treated blood" is then returned to the circulatory system of the host mammal. This method of treatment can be utilized in treating peripheral neuropathy in a human by the removal of M-proteins.

A diagnostic kit for the detection of the presence of antibodies in a liquid sample is also contemplated in this invention.

DETAILED DESCRIPTION OF PREFERRED EMBODIMENTS

The present invention relates to 3-sulfatoglucuronic acid-1-glycolipids as designated in Formula I.

The lipid tail in the compounds of the present invention contains a "backbone" chain that is about 4 to 30 atoms in length. The backbone chain of the lipid tail is a continuous, unbroken chain of carbon atoms, optionally containing heteroatom spacers interspersed along the chain, that extends from the 1-position of the 3-sulfatoglucuronic acid to the R group, and may comprise several hydrocarbon chain lengths separated by heteroatom spacers. The hydrocarbon chains in the lipid tail can include saturated and unsaturated hydrocarbons, and can be substituted with physiologically acceptable substituent groups, which are attached substituent radicals that do not interfere with the binding of the compound to the desired antibodies.

Exemplary heteroatom spacers that may be present in the lipid tail of the present invention are nitrogen, sulfur and oxygen.

The present invention preferentially relates to compounds which contain an alkyl chain attached to the 1-position of a 3-sulfatoglucuronic acid. These compounds have the formula:

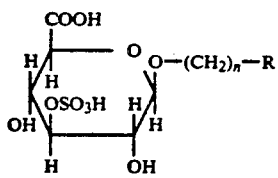

where n is an integer of about 4 to about 24 and R is a reactive functional group, as defined hereinafter. In a preferred embodiment, n is about 8 to about 12, more preferably 11, and R is a carboxy or lower alkoxycarbonyl group.

The term "reactive functional group" as used herein refers to chemical groups or radicals which characteristically participate in specific chemical reactions to form covalent bonds between the functional group and another chemical moiety.

Exemplary reactive functional groups or radicals, are lower alkylamine, lower alkenylamine, arylamine, primary amino, carboxy, aldehyde, ester, lower alkylcarbonyl, lower alkenylcarbonyl, arylcarbonyl, hydroxy, lower alkoxycarbonyl, aryloxycarbonyl, arylalkoxycarbonyl, vinylsulfonyl, sulfo, aziridinyl, epoxide, anhydride, mercapto, isocyanate, an active methylene-containing group, and an active halogen-containing group.

As used herein, the term "lower alkyl" includes $C_1$-$C_6$ alkyl groups, for example, methyl, ethyl, propyl, iso-propyl, n-butyl, sec-butyl, t-butyl, n-pentyl, 2-methyl-3-butyl, 1-methylbutyl, 2-methylbutyl, neo-pentyl, n-hexyl, 1-methylpentyl, 3-methylpentyl, 1-ethylbutyl, 2-ethylbutyl, 2-hexyl, 3-hexyl, and the like.

The term "lower alkenyl" includes $C_2$-$C_6$ alkene groups, for example, ethenyl, butenyl, pentenyl and the like.

The term "aryl" include aromatic rings that are fused, unfused or linked and can include one or more hetero atoms for example, phenyl, naphthyl, anthracenyl, biphenylyl, quinolyl and the like.

The term "lower alkoxycarbonyl" includes esters of a carboxy substituent formed with a lower alkyl alcohol where the lower alkyl portion of the alcohol is a lower alkyl radical, as described above. Exemplary esters are ethyl, methyl, t-butyl, neo-pentyl carboxylates, and the like. These esters can also be referred to as ethoxycarbonyl, methoxycarbonyl, t-butoxycarbonyl and neo-pentoxycarbonyl, respectively.

Exemplary lower alkylcarbonyl radicals include carboxymethyl, 2-carboxyethyl, 2-carboxyhexyl and the like. Exemplary lower alkoxycarbonyl lower alkyl radicals include 3-isopropoxycarbonylpropyl, 4-hexyloxycarbonylpentyl, and the like.

Exemplary lower alkenylcarbonyl radicals include vinylcarbonyl or acryloyl, maleic acid or cis-1,2-ethylenedicarboxylic acid and the like.

Examplary lower alkylamines are $C_1$-$C_6$ substituted primary and secondary alkylamines, such as methylamine, ethylamine, and ethylmethylamine. Exemplary lower alkenylamines are $C_2$-$C_6$ substituted primary and secondary amines, such as 2-butenylamine, methyl propenylamine and 2-butenylamine.

Exemplary active methylene-containing groups refer to groups of the form —(O=C)—$CH_2$—X, where X is a cyano, acyl or alkoxycarbonyl group where the alkyl portion of the acyl and alkoxycarbonyl groups contain about one to about 12 carbon atoms.

Active halogen-containing groups include halomethylaryl, halomethylcarbonyl, halomethylsulfonyl, haloethylcarbonyl, haloethylsulfonyl and halotriazinyl and the like.

A most preferred compound of the present invention is that represented by the structural formula:

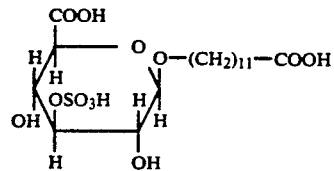

Also encompassed herein is a coated support that contains a compound of the present invention.

A "coated support", as used herein, includes a solid support to which is attached at least one molecule of a 3-sulfatoglucuronic acid compound of this invention. Attachment is by either physical means, such as adhesion, or chemical means, such as by covalent bonding. In the preferred embodiment, attachment is by chemical bonding, or linking at the R group. The solid support is preferably an inert, immobile material composed of glass, ceramic or polymer resins, and most preferably is in the form of a bead or fiber. The lipid portion of the molecule, e.g. $(CH_2)_n$, as designated in Formula I is easily attached to such solid support, as for example in an affinity column, through the R group.

The 3-sulfatoglucuronic acid compounds of the present invention bind to M-proteins, which are antibodies (IgM) produced from clones of plasma cells in peripheral neuropathies. The antibodies produced react with myelin and, specifically, with myelin associated glycoproteins (MAG). The compounds of the present invention mimic the antigenic site of myelin and MAG for M proteins.

Antibodies, such as M proteins, are removed from liquid samples in the processes of the present invention by contacting the liquid sample with a coated support containing a 3-sulfatoglucuronic acid compound of this invention. The liquid sample and coated support are maintained in contact for a time period sufficient to allow any antibodies, which possess affinity for the 3sulfatoglucuronic acid compound to bind to the coated support. The coated support with the antibodies bound thereto is then separated from the liquid sample.

As used herein, the term "antibodies" includes both molecules of a homologous monoclonal antibody, and multiple antibodies which each possess affinity for the compounds of the present invention. In a preferred embodiment, the antibodies removed from the liquid sample are M-proteins.

A method of treatment for antibody-related disorders such as peripheral neuropathy is encompassed in the present invention. In this method, blood is removed from a host mammal and placed into contact with a coated support which contains attached therein a compound of the present invention. The blood is maintained in contact with, or repeatedly circulated through, the coated support for a time period sufficient to allow antibodies present in the blood that possess affinity for the attached compound on the coated support to bind to the coated support, and thus produce a treated blood. The treated blood is then returned to the circulatory system of the host mammal. In a preferred embodiment the host mammal is a human.

In a most preferred embodiment of the present invention, blood is removed from a patient who has a peripheral neuropathy as a result of excess production of M-proteins. The blood is contacted, preferably through an extracorporeal circulating device, with an immobilized solid support to which molecules of a 1-glycolipid-3-sulfatoglucuronic acid compound of the present invention is attached. Contact is maintained between the coated support and the blood for a time period sufficient to effectuate binding of sufficient M-proteins to the 3-sulfatoglucuronic acid moeity to reduce their concentration to a non pathogenic level and thereby relieve the neuropathy. Following contacting, the blood is reinfused into the patient.

A method of detecting the presence of specific antibodies is contemplated wherein a liquid sample is contacted with the coated support of the present invention. Following separation from a liquid sample, such as blood, the coated support is washed free of extraneous material and is assayed to determine the presence of bound antibodies. Such an assay encompasses the use of a detection means capable of detecting the presence of an immunocomplex formed between the 3-sulfatoglucuronic acid compound of the coated support and the bound antibodies. In preferred embodiments, the detection means includes a label or indicating means capable of signaling the formation of an immunoreaction product.

As used herein, the terms "label" and "indicating means" in their various grammatical forms refer to single atoms and molecules that are either directly or indirectly involved in the production of a detectable signal to indicate the presence of an immunoreactant product. Such labels or indicating means are themselves well known in diagnostic chemistry and constitute a part of this invention only insofar as they are utilized with otherwise novel methods and/or systems.

In preferred embodiments, the detection group is an enzyme, such as horseradish peroxidase (HRP), glucose oxidase, or the like.

Radioactive elements are also useful labeling agents and are contemplated for use herein. A diagnostic system in kit form is also contemplated by the present invention. Such a kit includes, in an amount sufficient for at least one assay, a coated support of the present invention as a packaged reagent, as well as a detection means capable of detecting the presence of an immunocomplex formed from the 3-sulfatoglucuronic acid compound on the coated support of the invention and antibodies that immunoreact therewith, preferably as a separately packaged reagent. The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like. Instructions for use of the packaged reagent are also typically included.

As used herein, the term "package" refers to a solid matrix or material such as glass, plastic, paper, foil and the like capable of holding within fixed limits the coated support and a detection means such as an antibody composition or a monoclonal antibody composition.

The present invention thus contemplates a diagnostic system, preferably in kit form for assaying a sample. The sample is assayed for the presence of antibodies directed to an antigenic determinant which is mimicked by the 3-sulfatoglucuronic acid compounds of the present invention.

The system comprises: (1) at least one container that includes an effective amount of a coated support of the present invention, and (2) in a second container an indicating means capable of signaling the immunoreaction of antibodies from the sample to be assayed with the 3-sulfatoglucuronic acid moiety of the coated support of the present invention. The 3-sulfatoglucuronic acid compound, as designated in Formula I, may be supplied affixed to the solid matrix in an effective amount. It will be appreciated by those skilled in the art that an effective amount of antigen for carrying out different assays will vary with those assays and with the area of the solid matrix.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

The diagnostic systems can also include, preferably as a separate package, a specific binding agent. A "specific binding agent" is a molecular entity capable of selectively binding a reagent species of the present invention or an immunoreactant product containing such a species, but is not itself a composition of the present invention. Exemplary specific binding agents are second antibody molecules that immunoreact with the coated support-bound antibodies, complement proteins or fragments thereof, S. aureus protein A, and the like. Preferably, the specific binding agent binds the reagent species when that species is present as part of an immunoreaction complex.

The reagent species, labelled specific binding agent or amplifying regent of any diagnostic system described herein can be provided in solution, as a liquid dispersion or as a substantially dry powder, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

Having generally described this invention, a further understanding can be obtained by reference to certain specific examples which are provided herein for purposes of illustration only and are not intended to be limiting unless otherwise specified.

EXAMPLE 1

Preparation of
1-O-(11-hydroxycarbonylundecyl)-3-O-sulfate-beta-D-glucopyranosuronic acid (14)

(Step 1)

3-O-benzyl-D-glucopyranose (3) was prepared from commercial (Aldrich) diacetone-D-glucofuranose (1) according to a modified procedure of Finan & Warren, J. Chem. Soc. (1962), 3089, as follows:

To a mixture of 100 g of 1,2,5,6-diisopropylidene-D-glucofuranose (1) and 500 mL of benzyl chloride in a 3-neck round bottom flask, at room temperature, 120 g of freshly milled NaOH were added. The reaction mixture was heated to 98°-100° C. over 0.5 hours using a steam bath under vigorous magnetic stirring. After 0.5 hour, to the amber solution so produced was added another 120 g portion of milled NaOH, and the solution changed color to dark orange. After 6 hours the reaction was stopped, and the reaction mixture cooled to room temperature and diluted with 300 mL of water.

The solution was extracted with ether (5×500 mL) and the extract was washed with cold water until the aqueous layer was neutral according to litmus paper. The extract was dried over anhydrous sodium sulfate overnight and the solvent evaporated under reduced pressure (about 14 mm Hg) in a rotating evaporator. The excess of benzyl chloride was distilled off at 64° C./0.3 mm Hg. The yellow oil of 3-O-benzyl-1,2,5,6-diisopropylidene-D-glucofuranose (146 g) was distilled to a clear oil at 163°-164° C./0.28 mm Hg.

One third of the thus obtained oil (48.44 g) was dissolved in 20 mL of methanol, and 30 mL of 2N sulfuric acid was added. The clear solution was heated for 5 hours on a steam bath. The methanol was evaporated under reduced pressure of about 14 mm Hg in a rotating evaporator and the residual solution was diluted with 20 mL of water and heated on a steam bath for 1 hour. The solution was cooled to room temperature and neutralized to pH about 7 with the minimum amount of barium carbonate needed (basic ion exchange resin can be used instead). After concentration on the rotating evaporator, the yellow syrup was taken up in ethyl acetate and, on cooling, 3-O-benzyl-D-glucopyranose (3) slowly crystallized out.

(Step 2)

A solution of 5 g 3-O-benzyl-D-glucopyranose in 22 mL pyridine and 22 mL acetic acid was heated to nearly boiling, i.e., until bubbling began, and then allowed to cool to room temperature. Then the excess of pyridine was removed under reduced pressure. The residue was poured onto crushed ice and stirred with a glass stirring rod. The white precipitate of 3-O-benzyl-1,2,4,6-tetra-O-acetyl-D-glucopyranose (4) was filtered and washed several times with cold water and dried (yield 8.76 g).

(Step 3)

To 16 g of compound 4 in 35 mL of acetic acid precooled to 10° C., a solution of hydrogen bromide in acetic acid (50% w/v; 16 mL)-was added slowly. The solution was stirred at 5°-10° C. for 3 hours, diluted with alcohol-free chloroform (250 mL) then washed sequentially with ice water, aqueous sodium hydrogen carbonate, and water, and dried over magnesium sulfate. Removal of the solvent under reduced pressure gave a syrup which was taken up in methyl ether and adsorbed on silica gel (300 g). Elution with light petroleum ether gave 2.5 g of benzyl bromide, and further elution with ether gave a syrup of 3-O-benzyl-2,4,6-tri-O-acetyl-D-glucopyranosyl bromide (5)-which crystallized on cooling. Recrystallization from dry ether gave 12.2 g of needles with m.p. 79° C. and $[\alpha]_D^{25}$ +145 (c=1 in chloroform).

(Step 4)

Mercuric cyanide (2.2 g) and anhydrous calcium sulfate (7 g) were added to a solution of 11-methoxycarbonyl-undecanol (2 g)-in 50 mL of dry benzene. The mixture, protected from moisture and light in a reaction vessel equipped with septums and an inert atmosphere, and wrapped with aluminum foil, was stirred for 1 hour at room temperature prior to addition of compound 5 (1.98 g). The resulting reaction mixture was vigorously stirred for 4 days at room temperature. Dichloromethane (100 mL) was added, the solids were filtered off and the filtrate was sequentially washed with 10% (w/v) aqueous sodium chloride solution (50 mL), with saturated sodium bicarbonate (25 mL) and twice with water (50 mL). After drying over magnesium sulfate, the solvents were removed to leave a 1-O-(11-methoxycarbonylundecyl)-3-O-benzyl-2,4,6-tri-O-acetyl-$\beta$-D-glucopyranose (6)-syrup upon standing. Unfortunately the Rf of the product was exactly the same as the Rf of the starting lipid in most of the solvents used (and both were present).

(Step 5)

After careful drying in high vacuum, the crude product 6 was hydrolysed using a catalytic amount of sodium methylate in dry methanol. A clear new spot corresponding to 1-O-(11-methoxycarbonylundecyl)-3-O-benzyl-$\beta$-D-glucopyranose (7) appeared on the TLC (Thin Layer Chromatography) plate (Rf 0.1, hexane:ether=40:60). Approximately 2.8 g of the pure material was obtained after flash chromatography of the crude.

(Step 6)

Dry starting material 7 was dissolved in freshly distilled pyridine and dimethylformamide and excess (1.1 eq) of freshly crystallized trityl chloride was added together with catalytic amount of 4-dimethylaminopyridine. The reaction was carried out at room temperature under vigorous magnetic stirring. The course of the reaction was monitored by TLC. At this stage the tritylated product 1-O-(11-methoxycarbonylundecyl)-3-O-benzyl-6-O-triphenylmethyl-2,4-di-O-acetyl-$\beta$-D-glucopyranose (8), could be isolated (86% yield). However, in accordance with preferred practice, after completing the reaction, the reaction mixture was diluted with freshly distilled pyridine, and excess acetic anhydride was added at room temperature. When only traces of the starting material were detected according to TLC, the solvents were evaporated and the crude mixture was purified using flash chromatography on silica gel, affording 1-O-(11-methoxycarbonylundecyl)-3-O-benzyl-2,4-di-O-acetyl-$\beta$-D-glucopyranose (9). Total yield was 81% based on 7.-$^1$H NMR data ($\delta$, ppm, CDCl$_3$): 7.2-7.6 (20 H, arom.), 5.14 (tt, 2H CH$_2$OTr), 4.59 (s 2 H, CH$_2$Bn), 4.45 (d, 1 H, H-1 anom.), 3.52-3.94 (m, 4 H, carb. ring), 3.67 (s, 3 H, OCH$_3$), 3.16 (t, 2 H CH$_2$O lipid), 2.31 (t, 2 H, CH$_2$COO lipid), 2.03 (s 3 H, Ac), 1.70 (s, 3 H, Ac), 1.28-1.63 (18 H, lipid).

(Step 7)

A solution of 9 (200 mg) in 10 mL of dry dichloromethane was stirred at $-10°$ C. with 0.5 mL of dichloromethane saturated with HCl (gas). The reaction was completed in 20 minutes and the detritylated compound, 1-O-(11-methoxycarbonylundecyl)-3-O-benzyl-2,4-di-O-acetyl-$\beta$D-glucopyranose (10), was obtained in 80% yield using flash chromatography on silica gel.

(Step 8)

A solution of 10 (500 mg)-in 20 mL of water was vigorously stirred with freshly prepared platinum black (200 mg) at 85 C. while oxygen was slowly passed through the suspension. The pH of the reaction was maintained at approximately 8.0 with solid sodium bicarbonate. It took about 2 hours to complete the oxidation. The mixture was cooled after an additional 10 minutes of stirring. After removal of the catalyst by passing the solution through a Nylon-66 0.45 $\mu$m pore size filter, the filtrate was lyophilized. The residue was redissolved in 20 mL of ice-water and the solution was adjusted to pH 2 with 12N HCl and extracted with chloroform. The extract was washed with water until neutral, dried over sodium sulfate and concentrated, and the residue was esterfied with ethereal diazomethane. The product was eluted from a column of silica gel (Rf 0.45, hexane-ethyl acetate, 75:25) to give amorphous methyl 1-O-(11-methoxycarbonylundecyl)-3-O-benzyl-2,4-di-O-acetyl-$\beta$-D-glucopyranosuronate (11).$^1$H-NMR data: 7.26-7.30 (m, 5 H, arom.), 5.20 (t, 1 H), 5.08 (t,1 H), 4.62(s, 2 H, CH$_2$Bn), 4.45(d, 1 H, anom.), 3.85-3.97 (m, 2 H) 3.73 (s,3 H, COOMe), 3.68(s, 3 H, COOMe), 2.36(t, 2 H, CH$_2$ lipid), 1.98(s, 6 H, 2Ac), 1.20-1.63 (18 H, lipid).

(Step 9)

A solution of 11 (30 mg) in 2 mL of methanol was hydrogenated in the presence of 5% Pd/C (10 mg) for 24 hours. The reaction was monitored by TLC. The suspension was filtered and, after complete evaporation of the solvent and chromatography, pure methyl 1-O-(11-methoxycarbonylundecyl)-2, 4-di-O-acetyl-$\beta$-D-glucopyranosuronate (12) was obtained. The $^1$H NMR data confirmed the complete debenzylation.

(Step 10)

A solution of 12 (20 mg) in N,N-dimethylformamide (2 mL) was stirred for 12 hours at 50° C. in the presence of sulfur trioxide-triethylamine complex (20 mg). The mixture was then cooled, methanol (1 mL) was added, and the mixture was then eluted from a column of Sephadex LH-20 equilibrated with chloroform-methanol (1:1), using the same solvent. The product was eluted from a column of silica gel with ethyl acetate-pyridine-acetic acid-water (8:5:1:3) to yield a pure fraction, a solution of which in methanol (1 mL) was eluted from a column of Sephadex SP-25 (Na$^+$ form) with methanol-water (9:1) to afford methyl 1-O-(11-methoxycarbonylundecyl)-3-O-sulfate-2,4-di-O-acetyl-$\beta$-D-glucopyranosuronate monosodium salt (13) (90%). The $^1$H NMR data were consistent with the structure of compound 13. This material was used immediately for the next reaction and was not submitted for elemental analysis.

(Step 11)

A solution of 13 (2 mg)-in methanol-water (2:1, 1 mL) was saponified with 2.5M NaOH (0.2 mL) for 3 hours at room temperature. The mixture was diluted with aqueous methanol and 1-O-(11-hydroxycarbonylundecyl)-3-O-sulfate-$\beta$glucopyranosuronic acid trisodium salt (14) eluted successively from columns of Dowex 50 W (H$^+$, 20–50 mesh) and (Na$^+$, 20–50 mesh) resins with the same solvent. No destructive elemental analysis has been performed on this precious substance, but its highfield $^1$H-NMR spectrum demonstrated greater than 97% purity.

EXAMPLE 2

Alternate route for preparation of methyl-1-O-(11-methoxycarbonylundecyl)-3-O-benzyl-2,4-di-O-acetyl-beta-D-glucopyranosuronate (11)

A solution of compound 7 (500 mg) in 20 mL of water was vigorously stirred with freshly prepared platinum black (200 mg) at 85° C. while oxygen was slowly passed through the suspension. The pH of the reaction was maintained at approximately 8.0 with solid sodium bicarbonate. The reaction was completed in 2 hours. The mixture was cooled after an additional 10 minutes of stirring. After removal of the catalyst by passing the solution through a Nylon-66 0.45 $\mu$m pore size filter, the filtrate was lyophilized. The residue was acetylated with acetic anhydride, and the product was eluted from a column of silica gel (Rf 0.45, hexane-ethylacetate 75:25) to give amorphous 11 in a yield of 36%. $^1$H-NMR data: 7.26-7.3 (m, 5 H, arom.), 5.2 (t,1 H), 5.08 (t,1H), 4.62 (s, 2 H, CH$_2$Bn), 4.45 (d, 1 H, anom.), 3.85-3.97 (m, 2 H) 3.73 (s, 3 H, COOMe), 3.68 (s, 3 H, COOMe), 2.36 (t, 2 H, CH$_2$ lipid), 1.98 (s, 6 H, 2Ac), 1.20-1.63 (18 H, lipid).

EXAMPLE 3

Alternate route for preparation of methyl-1-O-(11-methoxycarbonylundecyl)-3-O-benzyl-2,4-di-O-acetyl-beta-D-glucopyranosuronate (11)

(Step 1)

A mixture of 3 (6 g)-and freshly purified chlorotriphenylmethane (5 g) in dry pyridine (50 mL) was heated for 2 hrs at 80° C. and then cooled to 0° C. 3-O-benzyl-6-O-triphenylmethyl-D-glucopyranose (16) could be isolated at this stage, or used further for acetylation. Acetic anhydride (15 mL)-was added, and the reaction mixture was heated at 80° C. until compound 16 had disappeared (TLC, ether:hexane, 1:2). The mixture was concentrated and a solution of the residue in chloroform (100 mL) was washed with aqueous potassium hydrogen sulfate and water, and concentrated. The crude 3-O-benzyl-6-O-triphenylmethyl-1,2,4-tri-O-acetyl-D-glucopyranose (17) was used in the next reaction. Small scale chromatography gave a material with $^1$H NMR data: 60:40 mixture of alpha:beta anomers 7.19–7.44 (m, 20 H, arom), 6.42 (d, 1 H, alpha-H)-, 5.67 (d, 1 H, beta-H), 3.07–5.23 (8 H), 2.17 (s, 3 H, Ac-alpha), 2.16 (s, 3H, Ac-beta) 2.01 (s, 3 H Ac-α, 1.99 (s, 3 H, Ac-beta), 1.69 (s, 3 H, Ac-β), 1.66 (s, 3 H, Ac-alpha).

(Step 2)

A solution of crude 17 in the minimum amount of dichloromethane was stirred at room temperature with aqueous 80% acetic acid (100 mL) until TLC demonstrated the disappearance of 17. Water was then added with stirring; the solid was removed and the filtrate was concentrated. The crude 3-O-benzyl-1,2,4-tri-O-acetyl-D-glucopyranose (18) was thus obtained; $^1$H NMR data: 60:40 mixture of anomers 6.32 (d, 1 H, alpha-H), 5.64 (d, 1 H, beta-H). A solution of the crude residue 18 in acetone was cooled to $-5°$ C. and a solution of chromium trioxide in 3.5M sulfuric acid was added dropwise with stirring. The mixture was allowed to attain room temperature, and, after 5 hours at room temperature, was poured into ice-cold water and extracted with chloroform. The extract was washed with water and concentrated, and a solution of the crude methyl ester of 3-O-benzyl-1,2,4-tri-O-acetyl-D-glucopyranosuronic acid (19) in ether was esterified with ethereal diazomethane. The product was eluted from a column of silica gel with chloroform-ethyl acetate (20:10) to give 19 (54%). $^1$H NMR date: mixture of anomers alpha:beta=60:40; 7.23–7.36 (m, 5 H, arom.), 6.38 (d, 1 H, alpha-H), 5.69 (d, 1 H, beta-H), 3.72 (s, 3 H, alpha-COOMe), 3.71 (s, 3 H, beta-COOMe), 1.96–2.16 (9 H, Ac).

(Step 3)

Bromination of compound 19 was carried out under similar conditions to those used in the preparation of 5 to produce methyl (3-O-benzyl-2,4-di-O-acetyl-α-D-glucopyranosyl bromide) uronate (20).

(Step 4)

Methyl 1-O-(11-methoxycarbonylundecyl)-3-O-benzyl-2,4-di-O-acetyl-B-D-glucopyranosuronate (11) is produced by the Konigs Knorr procedure, as described in the preparation of 6.

EXAMPLE 4

Preparation of 1-O-(8-hydroxycarbonyloctyl)-3-O-sulfate-beta-D-glucopyranosuronic acid trisodium salt (21)

Substitute methoxycarbonyloctanol for compound 1 in Example 1 and carry out the procedural steps 1 through 11 to produce the title compound.

EXAMPLE 5

Preparation of 1-O-(11-aminoundecyl)-3-O-sulfate-beta-D-glucopyranosuronic acid

The title compound is prepared by the method as described in Example 1, by substituting N-tert-butyloxycarbonyl-11-amino decanol for compound 1.

The foregoing specification, including the specific embodiments and examples, is intended to be illustrative of the present invention and is not to be taken as limiting. Numerous other variations and modifications can be effected without departing from the true spirit and scope of the present invention.

We claim:

1. A 3-sulfatoglucuronic acid derivative represented by the structural formula:

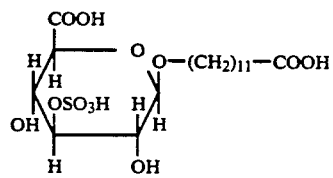

2. A compound represented by the structural formula:

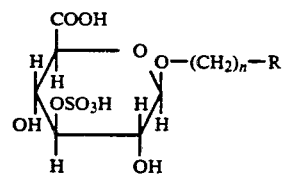

wherein n is 11 and R is a methoxycarbonyl group.

* * * * *